(12) United States Patent
Carriero et al.

US010836792B2

(10) Patent No.: US 10,836,792 B2
(45) Date of Patent: Nov. 17, 2020

(54) RETRO-INVERSO PEPTIDE INHIBITORS OF CELL MIGRATION, EXTRACELLULAR MATRIX AND ENDOTHELIAL INVASION BY TUMOR CELLS

(71) Applicant: ISTITUTO NAZIONALE TUMORI IRCCS "FONDAZIONE G. PASCALE", Naples (IT)

(72) Inventors: Maria Vincenza Carriero, Naples (IT); Gennaro Ciliberto, Rome (IT); Katia Bifulco, Boscotrecase (IT); Antonello Pessi, Rome (IT)

(73) Assignee: ISTITUTO NAZIONALE TUMORI IRCCS "FONDAZIONE G. PASCALE", Naples (IT)

( * ) Notice: Subject to any disclaimer, the term of this patent is extended or adjusted under 35 U.S.C. 154(b) by 0 days.

(21) Appl. No.: 16/092,584

(22) PCT Filed: Apr. 6, 2017

(86) PCT No.: PCT/EP2017/058267
§ 371 (c)(1),
(2) Date: Oct. 10, 2018

(87) PCT Pub. No.: WO2017/178333
PCT Pub. Date: Oct. 19, 2017

(65) Prior Publication Data
US 2019/0135863 A1   May 9, 2019

(30) Foreign Application Priority Data

Apr. 11, 2016   (EP) ..................... 16164615

(51) Int. Cl.
| | | |
|---|---|---|
| *C07K 5/107* | (2006.01) |
| *C07K 5/10* | (2006.01) |
| *C07K 5/09* | (2006.01) |
| *A61P 35/00* | (2006.01) |
| *A61K 51/08* | (2006.01) |
| *A61K 38/00* | (2006.01) |

(52) U.S. Cl.
CPC .......... *C07K 5/1016* (2013.01); *A61K 51/088* (2013.01); *A61P 35/00* (2018.01); *C07K 5/0817* (2013.01); *C07K 5/1002* (2013.01); *C07K 5/1027* (2013.01); *A61K 38/00* (2013.01); *Y02A 50/395* (2018.01)

(58) Field of Classification Search
None
See application file for complete search history.

(56) References Cited

U.S. PATENT DOCUMENTS

2015/0152139 A1*   6/2015   Hantash .................. A61P 17/00
514/18.6

FOREIGN PATENT DOCUMENTS

WO   2008017372 A1   2/2008

OTHER PUBLICATIONS

Pahwa et al., "Chronic Inflammation", StatPearls-NCBI Bookshelf, updated Jun. 4, 2019, pp. 1-8 (Year: 2019).*
Pimenta et al. ,"Design of Inhibitors for Human Tissue Kallikrein Using Non-Natural Aromatic and Basic Amino Acids", Biol. Chem., pp. 853-857; 2002 (Year: 2002).*
Mahalakshmi et al., "The Use of D-Amino Acids in Peptide Design", D-Amino Acids: A New Frontier in Amino Acid and Protein Research, 2006; pp. 415-430 (Year: 2006).*
Murdoch et al., "Chronic inflammation and asthma", Mutation Research, 2010, pp. 24-39 (Year: 2010).*
Chakravarty et al., "Positron Emission Tomography Image-Guided Drug Delivery: Current Status and Future Perspectives", Molecular Pharmaceutics, 2014, pp. 3777-3797 (Year: 2014).*
Marshall, K.M., et al., "Retro-inverso forms of gastrin5-12 are as biologically active as glycine-extended gastrin in vitro but not in vivo", Peptides 74 (2015) 16-22.
Search Report and Written Opinion of PCT/EP2017/058267 dated Jun. 14, 2017.

* cited by examiner

*Primary Examiner* — Lianko G Garyu
(74) *Attorney, Agent, or Firm* — Silvia Salvadori, P.C.; Silvia Salvadori

(57) ABSTRACT

The present invention discloses retro-inverso peptides and pharmaceutical composition containing them. The peptides of the invention prevent key events occurring during the metastatic process, i.e. invasion of the extracellular matrix, formation of a capillary network, and the entry into bloodstream. They are therefore useful in the treatment of diseases and conditions that are sustained by an increase of cell motility, cell invasion, and/or angiogenesis, such as tumors and chronic inflammation.

8 Claims, 11 Drawing Sheets
Specification includes a Sequence Listing.

EXAMPLE 2.

EXAMPLE 3.

EXAMPLE 10.

EXAMPLE 11.

RETRO-INVERSO PEPTIDE INHIBITORS OF CELL MIGRATION, EXTRACELLULAR MATRIX AND ENDOTHELIAL INVASION BY TUMOR CELLS

This application is a U.S. national stage of PCT/EP2017/058267 filed on 6 Apr. 2017, which claims priority to and the benefit of Italian Application No. 16164615.3 filed on 11 Apr. 2016, the contents of which are incorporated herein by reference in their entireties.

The present invention concerns retro-inverso peptides useful in the treatment of diseases and conditions that are sustained by an increase of cell motility, cell invasion, and/or angiogenesis, such as tumors and chronic inflammation.

BACKGROUND OF THE INVENTION

Despite significant progress regarding potential therapeutic targets aimed at improving survival, patients affected by solid tumors frequently die for systemic spread of the disease to distant sides. Indeed, currently available cancer therapies are limited by progression to a phenotype resistant to cytotoxic therapies, and by consequent uncontrolled tumor spread and metastatic dissemination. When cancer cells acquire the ability to separate and move away from the primary tumor mass, migrate through the surrounding tissue, and enter the lymphatic system and/or blood circulation, the prognosis becomes poor. To metastasize, tumor cells have to acquire early the ability to move and respond to motogen gradients. Therefore, the control of cell motility is a new and attractive approach for the clinical management of metastases. The development of metastases is a multistep process that requires active and specifically localized extracellular proteolysis as well as the activation of a series of physiological and biochemical processes that govern the migration from the primary tumor site, the invasion through the basement membrane, the entry of metastatic cells into the blood vessels, and finally, localization to the second site [1]. Cell migration is a spatially and temporally coordinated multistep process that orchestrates physiological processes such as embryonic morphogenesis, tissue repair and regeneration, and immune-cell trafficking [2]. When cell migration is deregulated, it contributes to numerous disorders including tumor metastasis, chronic inflammation, and vascular disease [3-4]. Migrating cells respond to growth factors, cytokines and chemokines, through the acquisition of a polarized morphology, the extension of adhesive protrusions, the attachment of the protrusion to substratum, the translocation of the cell body and finally, the detachment of the trailing end of the cell from the substratum [5-6]. This complex process requires the coupling of extracellular signals with the internal signalling machinery that controls cytoskeleton dynamics [7].

The clinical relevance of the urokinase receptor (uPAR) as a prognostic marker in human cancers is well documented, and high levels of soluble forms of uPAR in serum have been found to be associated with poor prognosis and increased risk of metastasis [8]. Also, uPAR plays an important role in the regulation of leukocyte trafficking [9]. uPAR is a glycosylated glycosyl-phosphatidyl-inositol-anchored protein [10], formed by 3 domains (DI, DII, and DIII) connected by short linker regions [11]. Besides being responsible for focalizing urokinase-mediated plasminogen activation on cell surface [12], uPAR also promotes intracellular signalling, thus regulating physiologic processes such as wound healing, immune responses, and stem cell mobilization, as well as pathologic conditions such as inflammation and tumor progression [9, 13]. uPAR is a widely recognized master regulator of cell migration through the assembly in composite regulatory units with transmembrane receptors including the Formyl Peptide Receptors type 1 and 2 (FPR)s and integrins [14]. Due to the pleiotropic nature of its interactors, uPAR represents both a challenge and an opportunity for targeting this receptor, and multiple therapeutic approaches have emerged. However, despite significant activity in this regard, no uPAR targeted therapeutic agent has advanced into clinical evaluation to date. This supports the relevance of innovative, therapeutic approaches devoted to interfering with uPAR/co-receptor interactions. A crucial signaling region of uPAR is the ($uPAR_{84-95}$) sequence that triggers cell migration and angiogenesis in vitro and in vivo by interacting with FPR1, even in the form of synthetic peptides [15-16].

FPRs are a family of 7-transmembrane, Gi-protein-coupled receptors that exert multiple functions in many pathophysiologic processes because of their capacity to interact with a variety of structurally diverse, chemotactic ligands [17-18]. Human FPR1, originally identified in neutrophils, monocytes and macrophages, elicits many responses upon ligation of formyl-peptide ligands derived from bacteria and mitochondria, including morphological polarization, locomotion, production of reactive-oxygen species and release of proteolytic enzymes [19]. In recent years, FPR1 has been shown to be expressed also in several non-myelocytic cells, suggesting other unidentified functions independent of the inflammatory response. Accumulating evidence demonstrates that FPR1 is also involved in the tumor progression of solid tumors, including glioblastoma, sarcoma, melanoma, ovarian, hepatic and lung carcinomas [19-22]. Therefore, FPR1 is a potential therapeutic target for the treatment of malignant human cancer and inflammation diseases.

uPAR derived peptides which prevent the interaction of uPAR with FPRs, and with the alpha chain of the vitronectin receptor have been reported [23-26]. Tetra- and pentapeptides that inhibit cell migration in vitro and have antitumoral action in vivo are disclosed in WO2008017372 A1. However, many of the prior art peptides are unstable to enzymatic digestion, which limits their half-life in vivo, whereas other peptides exhibit toxicity when administered in vivo, probably due to a low affinity binding site to alpha chain of the vitronectin receptor. Furthermore, the potent anti-angiogenic peptide Ac-L-Arg-Aib-L-Arg-D-Cα(Me)Phe-NH$_2$ (named UPARANT), which is stable in blood and displays prolonged resistance to enzymatic proteolysis, does not inhibit sarcoma cell invasion in a mouse model of lung colonization [26].

It remains therefore an unmet medical need to develop new peptides which prevent the interaction of uPAR with FPRs, which are resistant to proteolysis, and are not toxic when administered in vivo.

One general approach to overcome the susceptibility to degradation by proteases, which can substantially limit the duration of action in vivo of the peptides described so far [23-26], is the application of the Retro-Inverso (RI) concept [27-30]. In a RI analog, the sequence of the parent peptide is inverted, and the chirality of all the amino acids is changed from L to D. This results in a high degree of topochemical equivalence between the side-chains of the parent peptide and its RI analog, while the backbone amide bonds are inverted (FIG. 1). In a total RI modification, all the amide bonds are reversed, while in a partially modified RI analog only some of the amide bonds are inverted. When the interaction of the parent peptide with its receptor is dominated by side-chain interactions, the biological activity of the RI analog can be maintained, while the all-D-amino acid composition ensures stability to proteases. Several examples of successful application of the RI concept have been reported [32-41].

However, inversion of the amide backbone may result in loss of key main chain hydrogen bonds, and the conformational preferences of the parent and RI peptides may be different [31], an effect which is sequence-specific. It is not possible therefore to predict a priori if biologically active RI analogs of known peptide inhibitors of the uPAR-FPRs-vitronectin receptor interaction may be identified, and if so which are the most preferred RI sequences.

DESCRIPTION OF THE INVENTION

Figure 1:
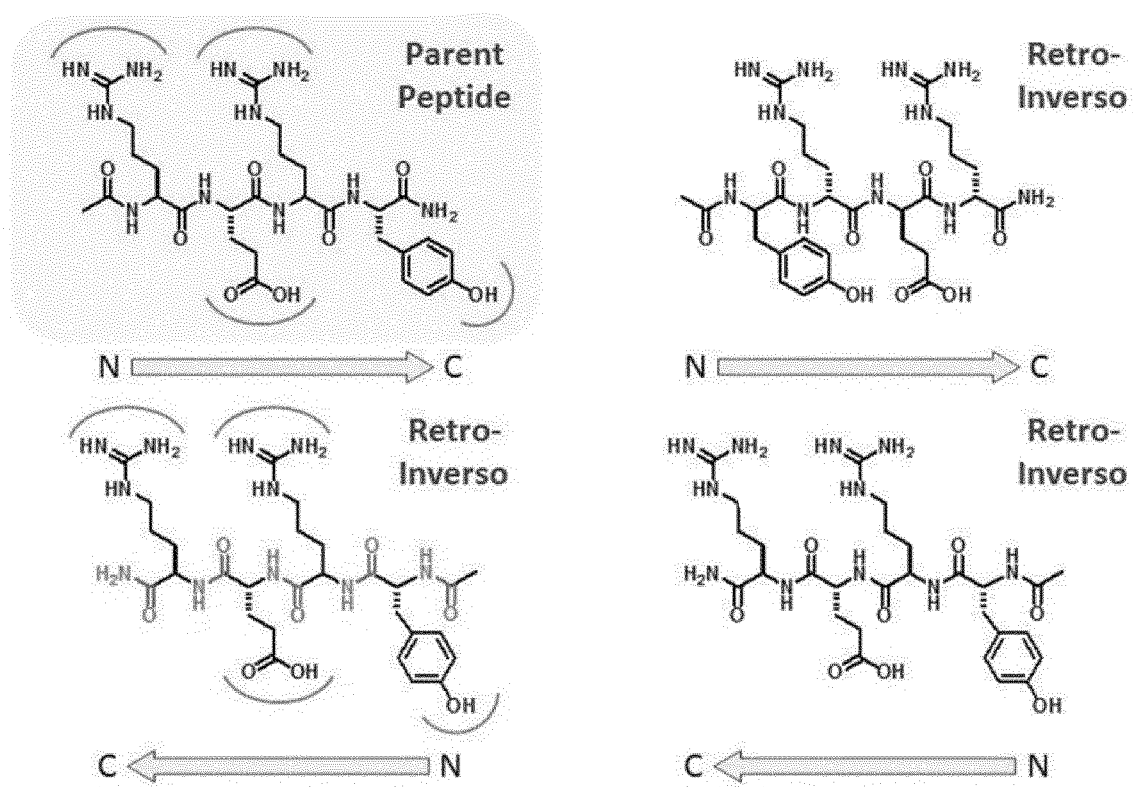
FIG. 1 High degree of topochemical equivalence between the side chains of a parent peptide and its Retro-Inverso (RI) analogs.

Object of the present application, are retro-inverso (RI) peptides that are potent inhibitors of cell migration, invasion and angiogenesis, and are stable in human serum.

The RI peptides of the invention have the following general formula (I):

$$X_1\text{-(D)-Arg-}X_2\text{-(D)-Arg-NH}_2 \qquad (I)$$

wherein:

$X_1$ is selected from the group consisting of Ac-(D)-Tyr, phenylacetyl and 3-phenylpropionyl;

$X_2$ is selected from the group consisting of (D)-Glu, (D)-Ser and Aib, wherein Aib is α-methyl-Ala;

and their pharmaceutically acceptable salts.

Preferred compounds of the invention (Table) are:

Ac-(D)-Tyr-(D)-Arg-(D)-Glu-(D)-Arg-NH$_2$ (RI-1), Ac-(D)-Tyr-(D)-Arg-(D)-Ser-(D)-Arg-NH$_2$ (RI-2), Ac-(D)-Tyr-(D)-Arg-Aib-(D)-Arg-NH$_2$ (RI-3), PhCH$_2$CO-(D)-Arg-Aib-(D)-Arg-NH$_2$ (RI-4) and PhCH$_2$CH$_2$CO-(D)-Arg-Aib-(D)-Arg-NH$_2$ (RI-5), and pharmaceutically acceptable salts thereof.

The compounds R1-1, RI-2 and RI-3 are the RI analogues of previously described peptides [24-26], whereas the compounds RI-4 and RI-5 are tripeptide analogs of Ac-(D)-Tyr-(D)-Arg-Aib-(D)-Arg-NH$_2$ (RI-3) where the acetylated aromatic amino acid (D)-Tyr is replaced by an achiral aromatic end-capping group (phenylacetyl or 3-phenylpropionyl) linked to the preceding amino acid.

The peptides of the invention may be prepared using the methods disclosed in the literature, such as Schroeder et al. "The Peptides" vol 1, Academic Press, 1965; Bodanszky et al. "Peptide Synthesis Interscience Publisher, 1966; Barany & Merrifield, "The peptides; Analysis, Synthesis, Biology", 2, Chapter 1, Academic Press, 1980 (25-26). These techniques include solution or solid-phase synthesis of peptides, organic chemistry synthetic methodologies, or any combination thereof. The synthetic protocol that is followed depends on the specific peptide to be synthesized. Preferably, methodologies based on the appropriate combination of solid-phase techniques and classical methods in solution are used that entail low production costs, especially on an industrial scale. Specifically, such methodologies consist in (i) solution synthesis of fragments of the peptide chain though the sequential coupling of properly activated N-protected amino acids to an amino acid or a to C-protected peptide chain, with isolation of the intermediates, subsequent selective deprotection of the C- and N-terminus of said fragments and, where necessary, of the side chains, until the desired peptide is obtained; (ii) solid-phase synthesis of the peptide chain from the C terminus to the N-terminus on an insoluble support. The peptide is removed from the resin by hydrolysis with anhydrous hydrofluoric acid or with trifluoroacetic acid in the presence of suitable scavengers.

The compounds of the invention do not have additional low affinity binding site with the alpha chain of the integrin, and exhibit unexpected inhibitory activity in preventing in vitro and in vivo extracellular invasion and vascular infiltration by tumor cells. They also inhibit trans-endothelial migration of monocytes. They recognize FPR1 with high affinity, thus preventing uPAR/FPR1 interaction. The compounds of the invention are able to prevent in vitro migration and extracellular matrix invasion of a variety of human cancer cells, including sarcoma, melanoma and ovarian cancer cells. In vitro, RI-3 is able to reduce the capability of sarcoma, melanoma and ovarian cancer cells to cross endothelial monolayers. In vivo, when administrated i.p. at 6 mg/Kg every day for 10 days, RI-3 reduces the growth and vascularization rate of tumors formed by human sarcoma cells injected subcutaneously in the flanks of nude mice, with no signs of toxicity. Consistently, RI-3 reduces by 74.5% the number of circulating sarcoma cells in the murine blood samples. In line with its ability to counteract Vascular Endothelial Growth Factor-induced tube formation of endothelial cells in vitro, RI-3 reduces vascularization rate of tumors formed by human sarcoma cells injected subcutaneously in the flanks of nude mice.

Since the retro-inverso peptides of the present invention prevent three key events occurring during the metastatic process: invasion of the extracellular matrix, formation of a capillary network, and the entry into bloodstream, they can be used in the prevention and treatment of cancer, in particular in the prevention and treatment of the local or metastatic invasion of malignant tumours such as sarcoma, breast, lung and ovary carcinoma, melanoma and glioblastoma.

The compounds of the invention are also useful in the prevention and treatment of disorders related to neo-angiogenesis and neo-vascularization, such as Kaposi's sarcoma, and in the prevention and treatment of disorders associated with altered cellular motility such as auto-immune diseases and chronic inflammations, such as rheumatoid arthritis, psoriasis and chronic granulomatous disease.

For the intended uses, the compounds of the invention can be administered as such, or in the form of salts, in pharmaceutical compositions that can be administered by the oral, parenteral, topic, airway (aerosol) or transdermal route, optionally in association with other active ingredients. The unit dose in humans may vary within a wide range, typically from 0.1 μg to 1 g per dose, preferably from 0.1 mg to 100 mg, which can be easily determined by the physician depending on the pathology, the severity of the disease, and weight, sex and age of the patient. Said pharmaceutical compositions can be prepared by conventional methods and can contain suitable vehicles and/or excipients.

The compounds of the invention can also be radiolabeled with a positron emitter for microPET imaging and can therefore be used as theranostic agents, i.e. for the diagnosis, detection, screening and/or staging of tumors; for therapy monitoring and/or treatment evaluation; for real-time tumor imaging, such as for the visualization of tumor boundaries during surgery.

The following examples illustrate the invention in a greater detail.

EXAMPLE 1. SYNTHESIS OF THE RETRO-INVERSO PEPTIDES RI-1, RI-2, RI-3, RI-4, RI-5

The RI Peptides shown in Table were synthesized on solid-phase with Fmoc/t-Bu chemistry, on an APEX 396 machine, using a Rink-amide PS resin (Chemimpex). Protected amino acids were dissolved at 0.5M concentration in 0.5M 1-hydroxybenzotriazole (HOBt) in N,N-dimethylformamide (DMF). Acylation was for 45 min with 5 molar excess of activated amino acid over the resin free amino groups. Activation was with equimolar O-(7-azabenzotriazol-1-il)-N,N,N',N'-tetramethyl-uronium hexafluorophosphate (HATU) e 2 equivalents of diisopropyl-ethylamine (DIEA), from a 2M solution in N-methylpyrrolidone (NMP). The protecting groups were t-Bu for (D)-Glu, (D)-Ser, and (D)-Tyr, and 2,2,4,6,7-pentamethyl-diidrobenzofuran-5-sulfonyl for D-Arg. At the end of the assembly, the peptides were acetylated with 10 equivalents of acetic anhydride, or reacted with 10 equivalents of Phenylacetic acid or 3-Phenylpropionic acid in the presence of 10 equivalents of DIEA. Cleavage with simultaneous release of the protecting groups was with 88% trifluoroacetic acid (TFA), 5% phenol, 2% triisopropylsilane, and 5% $H_2O$, for 2 h at 25° C. After filtering off the resin, the crude peptide was precipitated with cold tert-butyl ether (TBE) (50 mL/4 mL peptide solution), the precipitate was washed twice with TBE, and dried under vacuum. The dry precipitate was dissolved in 50:50 v/v $H_2O$/Acetonitrile and lyophilized.

The peptides were purified by reversed-phase HPLC on a preparative Waters XBridge C18 OBD column (30×150 mm, 5 μm, 100 Å), using as eluents (A) 0.1% TFA in $H_2O$ and (B) 0.1% TFA in acetonitrile. For peptides RI-1 and RI-3 the gradient used was: 10% (B) isocratic (5 min), 10%-25% (B) in 20 min, 25%-80% (B) in 3 min, 80% (B) isocratic (2 min); for peptides RI-2, RI-4, and RI-5, the gradient used was: 5% (B) isocratic (5 min), 5%-30% (B) in 20 min, 25%-80% (B) in 3 min, 80% (B) isocratic (2 min). The flow rate was 30 mL/min, and the monitoring wavelength was 214 nm. Fractions with >95% purity were pooled and lyophilized.

The purified peptides were characterized on an UPLC Waters instrument equipped with an electrospray Acquity SQ Detector and a BEH120 C18 Acquity column (Waters 2.1×100 mm, 1.7 μm) at 45° C., using as eluents (A) 0.1% TFA in $H_2O$ and (B) 0.1% TFA in acetonitrile. RI-1: MW (theor.) 663.7 Da, found $[M+H]^+$=664.4 Da; RI-2: MW (theor.) 621.3 Da, found $[M+H]^+$=622.3 Da; RI-3: MW (theor.) 619.7 Da, found $[M+H]^+$=620.5 Da; RI-4: MW (theor.) 533.1 Da, found $[M+H]^+$=533.5 Da; RI-5: MW (theor.) 547.1 Da, found $[M+H]^+$=547.5 Da.

TABLE

Sequence of the RI peptides of the present invention.

| Peptide | Sequence |
| --- | --- |
| RI-1 | Ac-(D)-Tyr-(D)-Arg-(D)-Glu-(D)-Arg-$NH_2$ |
| RI-2 | Ac-(D)-Tyr-(D)-Arg-(D)-Ser-(D)-Arg-$NH_2$ |
| RI-3 | Ac-(D)-Tyr-(D)-Arg-Aib-(D)-Arg-$NH_2$ |
| RI-4 | Phenylacetyl-D-Arg-Aib-D-Arg-$NH_2$ |
| RI-5 | 3-phenylpropionyl-D-Arg-Aib-D-Arg-$NH_2$ |

EXAMPLE 2. RETRO-INVERSO PEPTIDES DO NOT PROMOTE CELL MIGRATION

Figure 2:
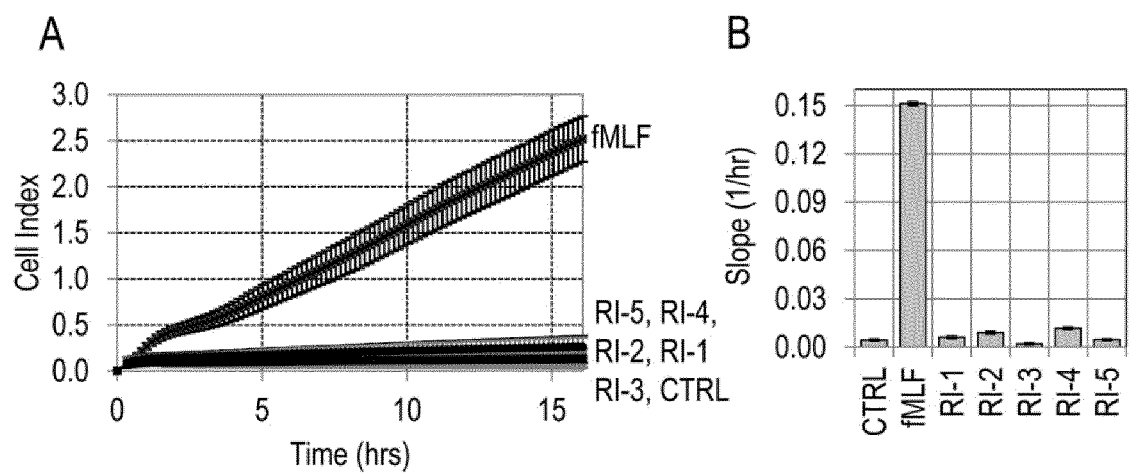
FIG. 2 Migration of human fibrosarcoma HT1080 cells toward 10 nM N-formyl-methionyl-leucyl-phenylalanine peptide (fMLF) or 10 nM of retro-inverso peptides, assessed in real-time for 18 hrs using the xCELLigence RTCA technology as described in Example 2. Cell index due to the adhesion of migrating cells to microelectrodes are reported in (A); analysis of slopes representing the change rate of cell index generated in the time range 0-12 hr are reported in (B).

We assessed whether new generated retro-inverso peptides elicit themselves cell migration of human fibrosarcoma HT1080 cells. Cell migration toward 10 nM N-formyl-methionyl-leucyl-phenylalanine peptide (fMLF) or 10 nM of the indicated retro-inverso peptides was monitored in real-time for 18 hrs using the xCELLigence RTCA technology, which records as cell index, changes due to the adhesion of migrating cells to microelectrodes. All peptides failed to trigger cell migration, except the peptide fMLF that, as expected, elicited a considerable cell migration. The results are depicted in FIG. 2. Data represent mean±SD from a quadruplicate experiment representative of 2 replicates (A). These results were confirmed by the analysis of slopes representing the change rate of cell index generated in the time range 0-12 hr (B).

EXAMPLE 3. RETRO-INVERSO PEPTIDE RI-3 INTERFERES WITH FPR1 BIOLOGICAL ACTIVITY BY BLOCKING AGONIST/FPR1 INTERACTION AND BY PREVENTING AGONIST-INDUCED FPR1 INTERNALIZATION

Figure 3:
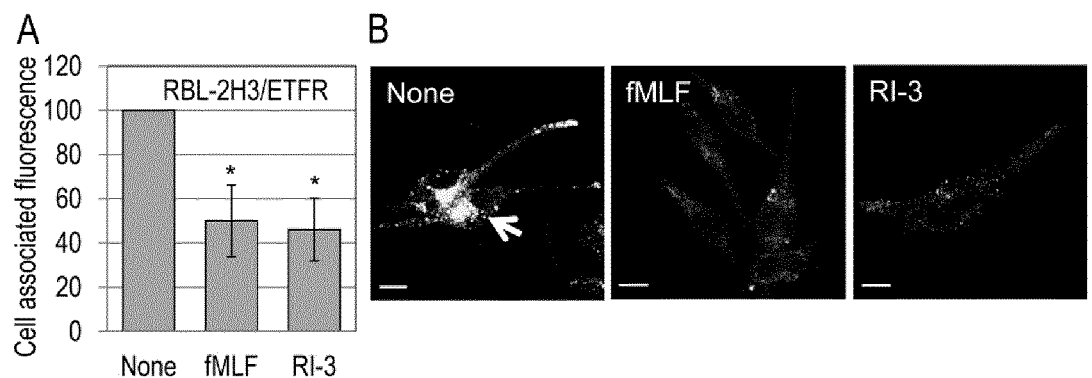
FIG. 3 The retro-inverso peptide RI-3 competes with fMLF for binding to FPR1 (A) and inhibits fMLF-triggered FPR1 internalization (B) in rat basophilic leukaemia RBL-2H3/ETFR cells (Example 3).

To test whether new generated peptides affect agonist-induced FPR1 activation, rat basophilic leukaemia RBL-2H3/ETFR cells stably expressing FPR1 [24], were pre-incubated with diluents, (None), 100 nM fMLF, or 100 nM RI-3 for 60 min at 4° C. (to avoid FPR1 internalization), and then exposed to 10 nM N-Formyl-Nle-Leu-Phe-Nle-Tyr-Lys-fluorescein (FITC-fMLF) for 60 min at 4° C. Cell-associated fluorescence was measured using a fluorescence plate reader. The results are depicted in FIG. 3. Data, expressed as a percentage of the fluorescence associated to cells exposed to FITC-fMLF alone (None=100%), represent mean±SD from an experiment performed in triplicate. *Statistical significance was calculated against None with $p<0.001$. FPR1 expressing RBL-2H3/ETFR cells exhibited a specific binding that was strongly reduced by unlabelled fMLF, as expected. The peptide RI-3 inhibited binding of fluorescent agonist to RBL-2H3/ETFR cells to a similar extent as compared to fMLF (A). To evaluate the effect of RI-3 on agonist-dependent FPR1 internalization, binding experiments were performed at 37° C. and cells were visualized using a Zeiss 510 Meta LSM microscope. Original magnifications: 630×. Scale bar: 10 μm. Upon exposure of RBL-2H3/ETFR cells to FITC-fMLF (None), FPR1 appeared mainly internalized as indicated by green fluorescent intra-cytoplasmic spots (arrow) which were prevented by cell pre-incubation with an excess fMLF, as expected. Similarly to fMLF, RI-3 prevented agonist-dependent FPR1 internalization (B). These findings indicate that retro-inverso peptide RI-3 competes with fMLF for binding to FPR1 and that RI-3 inhibits fMLF-triggered FPR1 internalization.

EXAMPLE 4. RETRO-INVERSO PEPTIDES INHIBIT CELL MIGRATION IN A DOSE DEPENDENT MANNER

Figure 4:
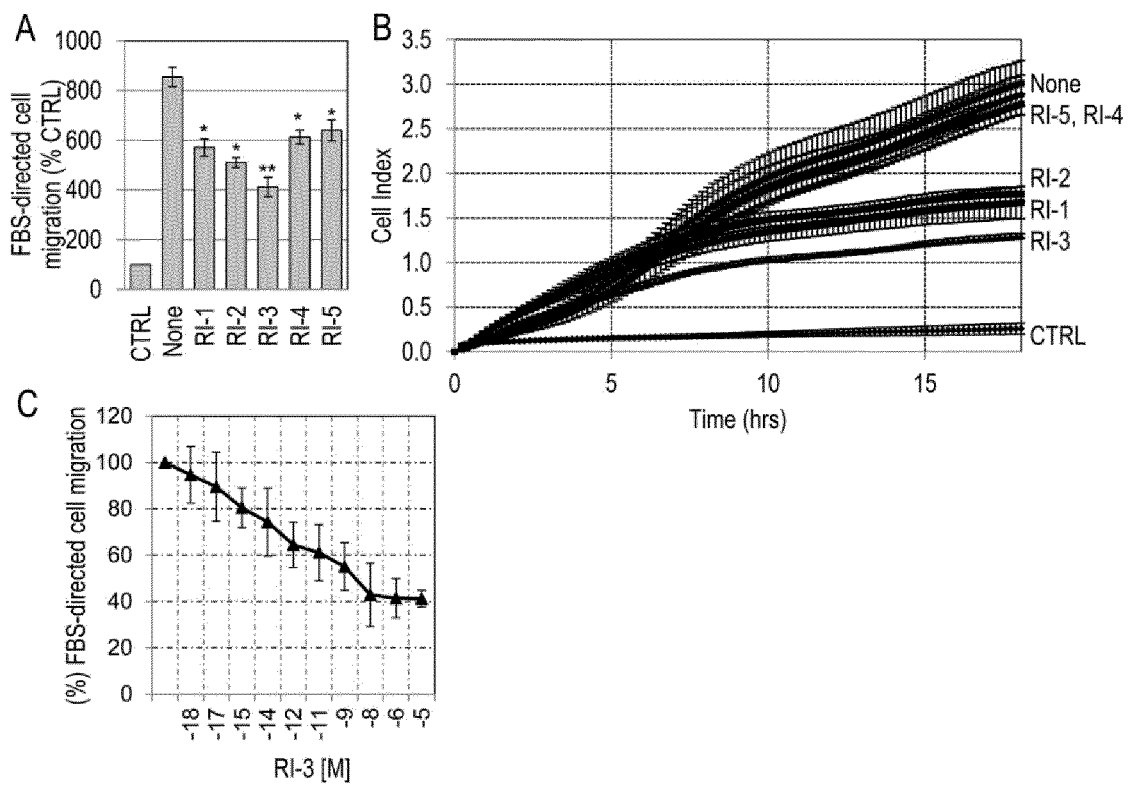
FIG. 4 Retro-inverso peptides inhibit FBS-directed migration of HT1080 cells in a dose dependent manner (Example 4).

To assess whether retro-inverso peptides exert some effect on directional cell migration, HT1080 cells were allowed to migrate for 4 hrs in Boyden chambers toward serum-free medium (CTRL), 10% FBS (None) or 10% FBS mixed with peptides, each tested at 10 nM concentration. The results are reported in FIG. 4. For quantitative analysis, the basal values assessed in the absence of FBS (CTRL) was taken as 100% and all values were reported relative to that. Data are the means±SD of two independent experiments, performed in triplicate. Statistical significance calculated against None with *$p<0.01$, **$p<0.001$ (A). All retro-inverso peptides caused a reduction of FBS-directed cell migration although to different extent. Peptides RI-1, RI-2, RI-3, RI-4 and RI-5 reduced by 49%, 46%, 65%, 9% and 6%, respectively, the extent of FBS-directed cell migration. Similar results were obtained when, HT1080 cell migration was monitored in real time for 18 hrs at 37° C., 5% $CO_2$ by the xCELLigence system. Data represent mean±SD from a quadruplicate experiment representative of 2 replicates (B). Then, HT1080 cells were allowed to migrate in Boyden chambers toward 10% FBS plus increasing concentrations of RI-3, and data were expressed as a percentage of cells migrated toward FBS alone (100%) Inhibitory effect of RI-3 is dose-dependent, it starts in the high fM range, it seems to level off in the nM range and reaches an overall 50% reduction at $1\times10^{-13}$M (C).

EXAMPLE 5. RETRO-INVERSO PEPTIDES INHIBIT CELL INVASION IN A DOSE DEPENDENT MANNER

Figure 5:
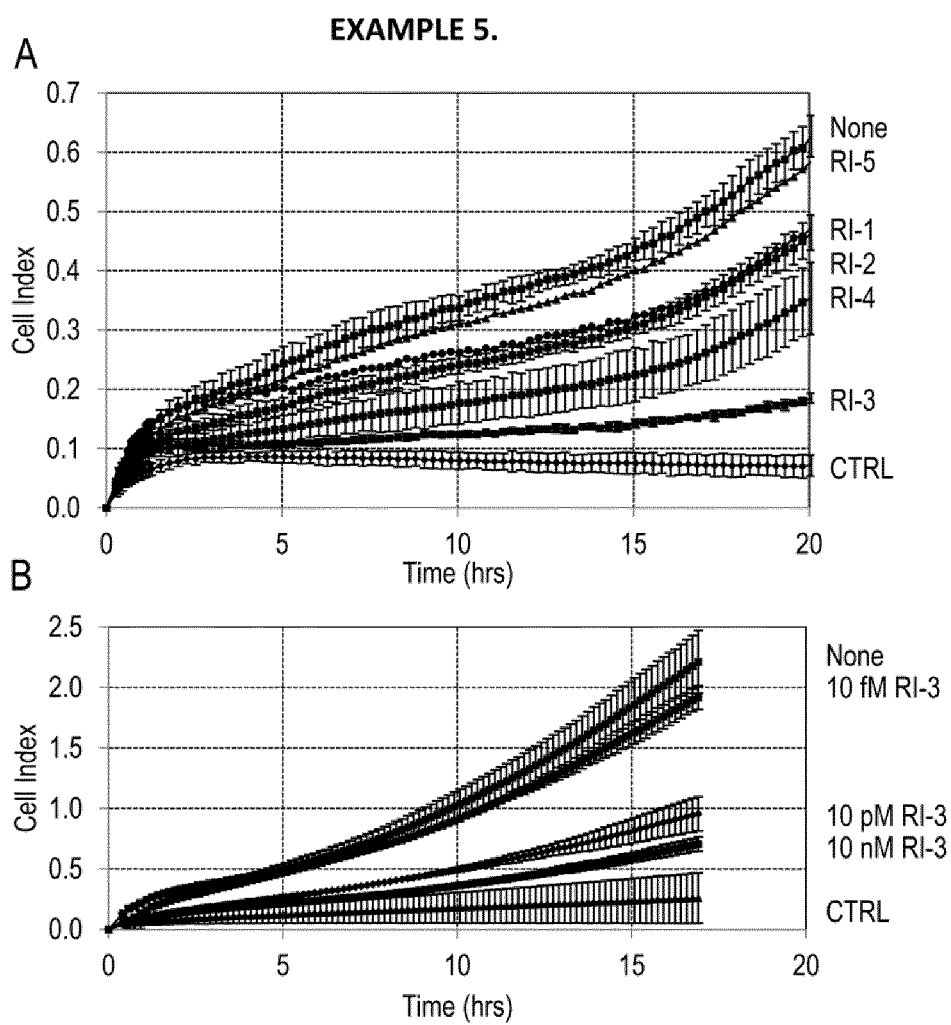
FIG. 5 Peptides RI-1, RI-2, RI-3, RI-4 and RI-5 reduced by 33%, 35%, 81%, 52% and 11%, respectively, the extent of FBS-directed matrigel invasion of HT1080 cells (A), as assessed in real time using the xCELLigence RTCA technology. The inhibitory effect of RI-3 is dose-dependent (B) (Example 5).

Cell migration is a prerequisite for cancer invasion. Therefore, we investigated whether retro-inverso peptides prevent matrigel invasion of HT1080 cells using the xCELLigence RTCA technology. Cells were seeded on polymerized matrigel and lower chambers were filled with DMEM (CTRL), growth medium (None) or growth medium with 10 nM the indicated peptides (A), or with increasing concentrations of RI-3 (B). Matrigel invasion was monitored in real time for 20 (A) or 18 (B) hrs at 37° C., 5% $CO_2$ and the impedance values were automatically monitored as changes in cell index. The results are reported in FIG. 5. Data represent means±SD from quadruplicate experiments, each representative of 2 replicates. HT1080 cells were able to cross matrigel in the presence of 10% FBS. All retro-inverso peptides caused a reduction of FBS-directed cell migration although to different extent. Peptides RI-1, RI-2, RI-3, RI-4 and RI-5 reduced by 33%, 35%, 81%, 52% and 11%, respectively, the extent of FBS-directed cell invasion (A) Inhibitory effect of RI-3 is dose-dependent maximal effect being reached in the nanomolar range (B).

EXAMPLE 6. RETRO-INVERSO PEPTIDE RI-3 DOES NOT AFFECT CELL PROLIFERATION

Figure 6:
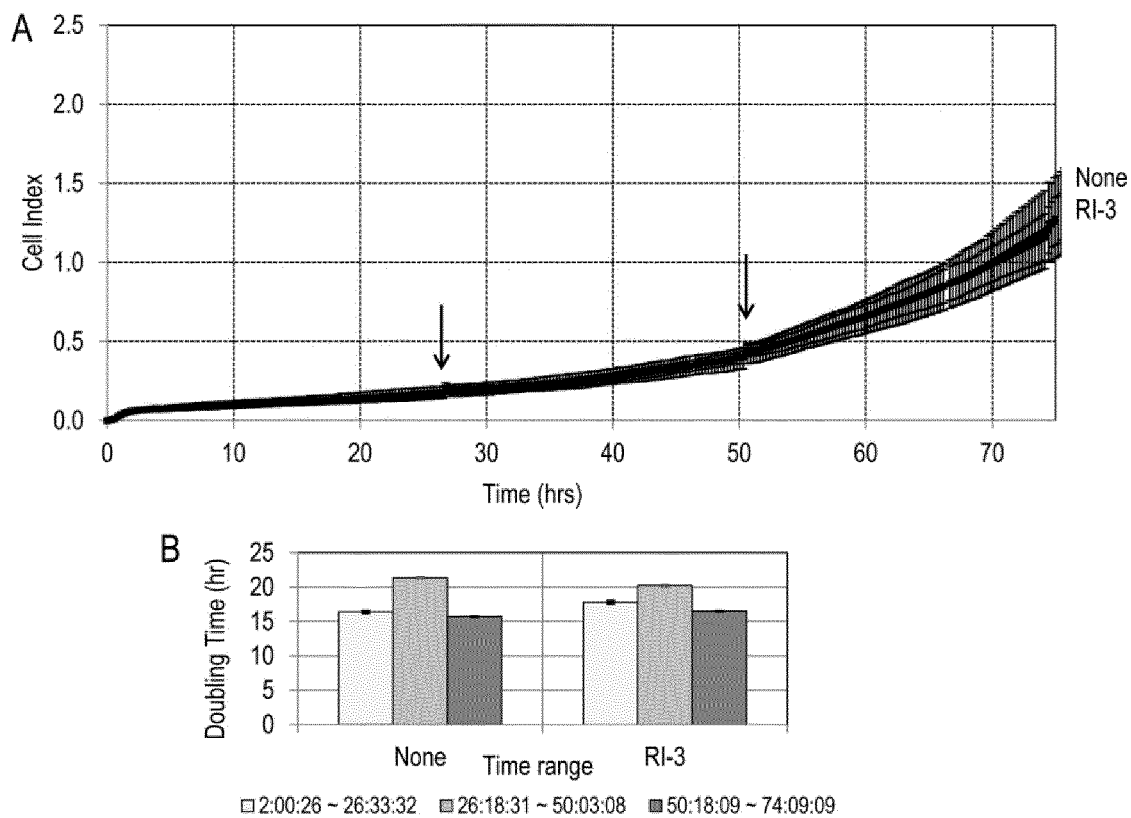
FIG. 6 The retro-inverso peptide RI-3 does not affect proliferation of HT1080 cells as assessed using the xCELLigence technology (Example 6).

Cell proliferation of HT1080 cells was monitored for 75 hrs using the xCELLigence technology. Cells ($1\times10^3$ cells/well) were seeded on E-plates in growth medium (None) or growth medium plus 10 μM RI-3 and allowed to proliferate at 37° C., 5% $CO_2$. Medium was replaced every 24 hrs (arrows). Impedance value of each well was automatically monitored and expressed as cell index. The results are reported in FIG. 6. Data represent mean±SD from a quadruplicate experiment representative of 2 replicates (A). HT1080 cells with/without 10 μM RI-3 exhibit comparable doubling times calculated during the exponential growth. In the 2-26 time range the doubling times of cells exposed to diluents or to RI-3 were 16.3828+/−0.22 hrs and 17.7648+/−0.27 hrs, respectively (B).

EXAMPLE 7. RETRO-INVERSO PEPTIDE RI-3 IS STABLE IN HUMAN SERUM

Figure 7:
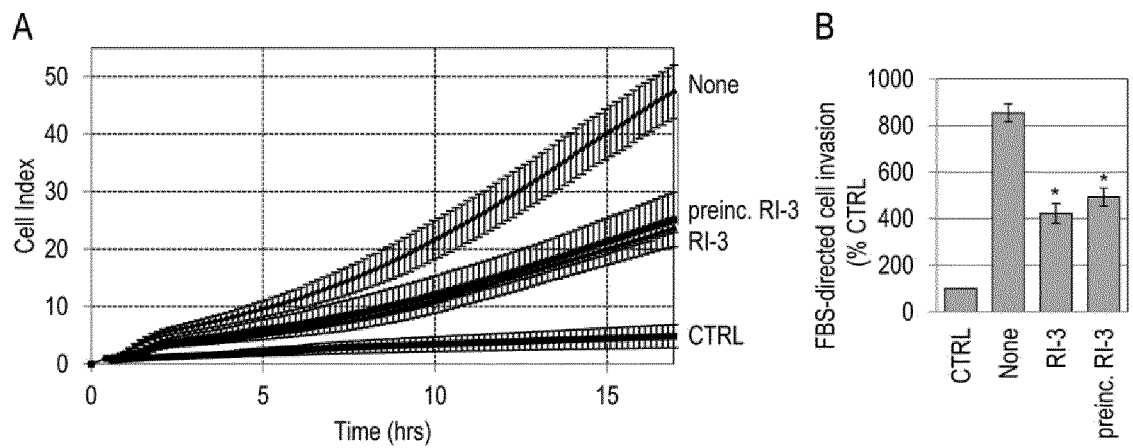
FIG. 7 The retro-inverso peptide RI-3 is stable when pre-incubated in bovine (A) or human serum (B) as assessed in real time using the xCELLigence technology (A) or in Boyden chambers (B) (Example 7).

The stability of the retro-inverso peptide RI-3 in bovine and human serum was investigated through incubation of the peptide at a $10^{-3}$ mol/L in serum for 18 hrs at 37° C. HT1080 cells were allowed to migrate toward DMEM (CTRL), 10% FBS (None), 10% FBS plus 10 nM RI-3 or 10% FBS with 10 nM RI-3 pre-incubated with bovine serum and the impedance values were automatically monitored in real time by the xCELLigence system for 18 hrs and expressed as cell index. The results are reported in FIG. 7. Data represent the means from a quadruplicate experiment representative of 2 replicates. Cell index values recorded by migrating cells exposed to RI-3 or RI-3 pre-incubated with bovine serum generated overlapping curves indicating that RI-3 is stable to enzymatic digestion (A). The stability of RI-3 in human serum was further investigated in cell invasion experiments performed in Boyden chambers. HT1080 cells were allowed to invade matrigel for 6 hrs, toward DMEM (CTRL), 10% FBS (None), 10% FBS plus 10 nM RI-3 or 10% FBS with 10 nM RI-3 pre-incubated with human serum. For quantitative analysis of cell invasion, the basal value assessed in the absence of FBS (CTRL) was taken as 100% and all values were reported relative to that. Data are the means±SD from a triplicate experiment. *Statistical significance was calculated against None with p<0.005. When pre-incubated with human serum, RI-3 retains the 81% of inhibitory activity (B).

EXAMPLE 8. RETRO-INVERSO PEPTIDE RI-3 PREVENTS MATRIGEL INVASION BY HUMAN SARCOMA, MELANOMA AND EPITHELIAL OVARIAN CARCINOMA CELLS

Figure 8:
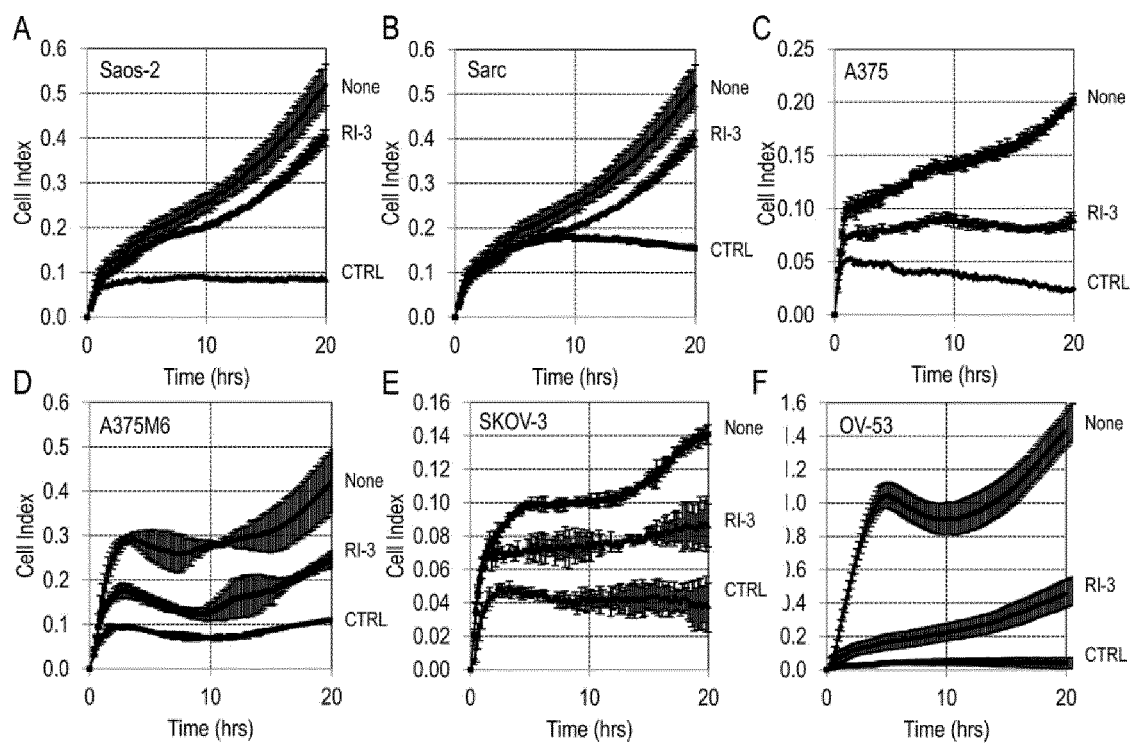
FIG. 8 At the concentration of 10 nM the retro-inverso peptide RI-3 prevents matrigel invasion of tumor cells from human osteosarcoma Saos-2 (A), chondrosarcoma Sarc (B), melanoma A375 (C), metastatic melanoma A375M6 (D), ovarian carcinoma SKOV-3 cells (E), or primary ovarian cancer cells derived from a tumor excision (OV-53) (F), as monitored in real-time for 20 hr as changes in cell index by the xCELLigence RTCA system (Example 8).

To investigate the ability of RI-3 to prevents matrigel invasion of tumor cells form different tissue origins, human osteosarcoma Saos-2 (A), chondrosarcoma Sarc (B) melanoma A375 (C), metastatic melanoma A375M6 (D), ovarian carcinoma SKOV-3 cells (E) or primary ovarian cancer cells derived from a tumor excision (OV-53) (F) were seeded on polymerized matrigel and allowed to invade matrigel in the absence (None) or in the presence of 10 nM RI-3. Cell invasion was monitored in real-time for 20 hrs as changes in cell index by the xCELLigence RTCA system. The results are reported in FIG. 8. Data represent mean±SD from quadruplicate experiments. All cell lines were able to cross matrigel, although to a different extent. In all case RI-3 reduced matrigel invasion by about 30%, 31%, 64%, 57%, 53% and 68%, of Saos-2, Sarc, A375, A375M6, SKOV-3 and OV-53 cells, respectively.

EXAMPLE 9. RETRO-INVERSO PEPTIDE RI-3 PREVENTS IN VITRO TRANS-ENDOTHELIAL MIGRATION BY SARCOMA, MELANOMA AND EPITHELIAL OVARIAN CARCINOMA CELLS AS WELL AS BY HUMAN MONOCYTES

Figure 9:
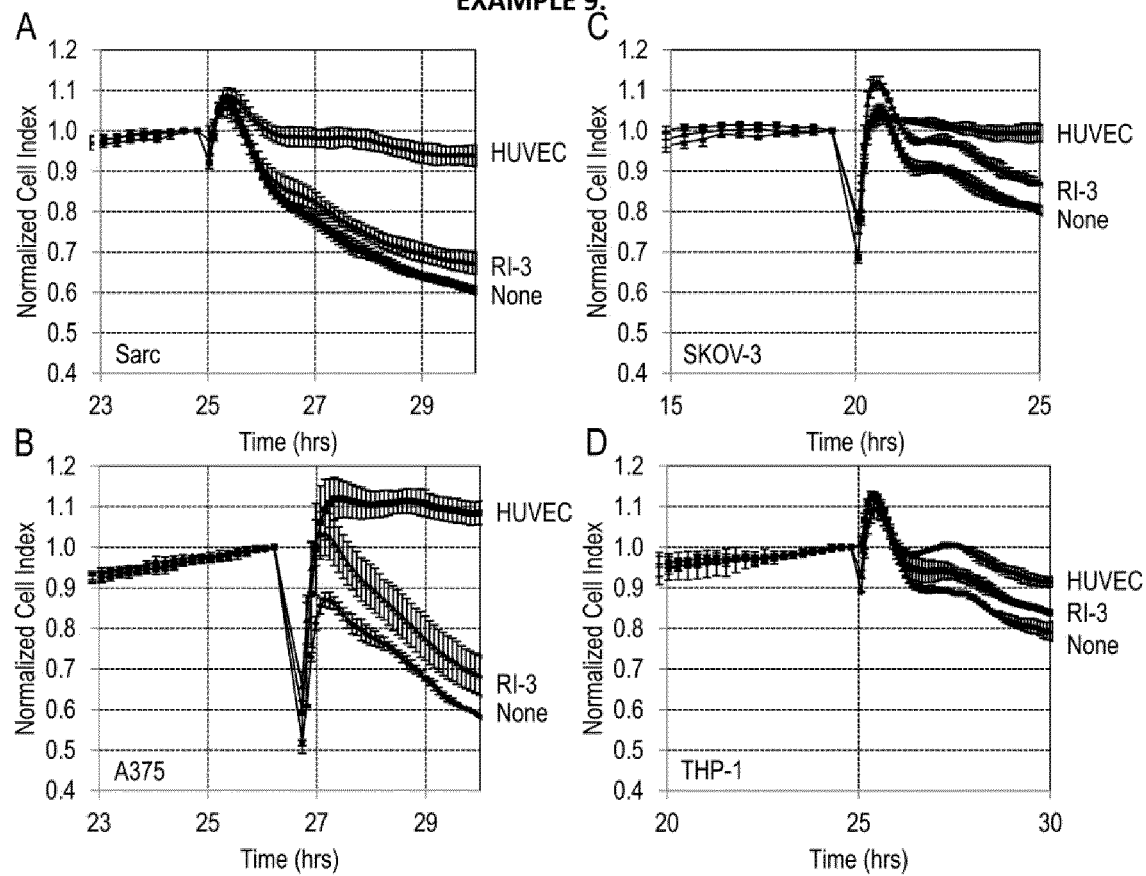
FIG. 9 At the concentration of 10 nM the retro-inverso peptide RI-3 affects trans-endothelial migration of human chondrosarcoma Sarc (A), melanoma A375 (B), ovarian carcinoma SKOV-3 (C) cells, or THP1 monocytes (D), as monitored by the xCELLigence RTCA system (Example 9).
Figure 10:
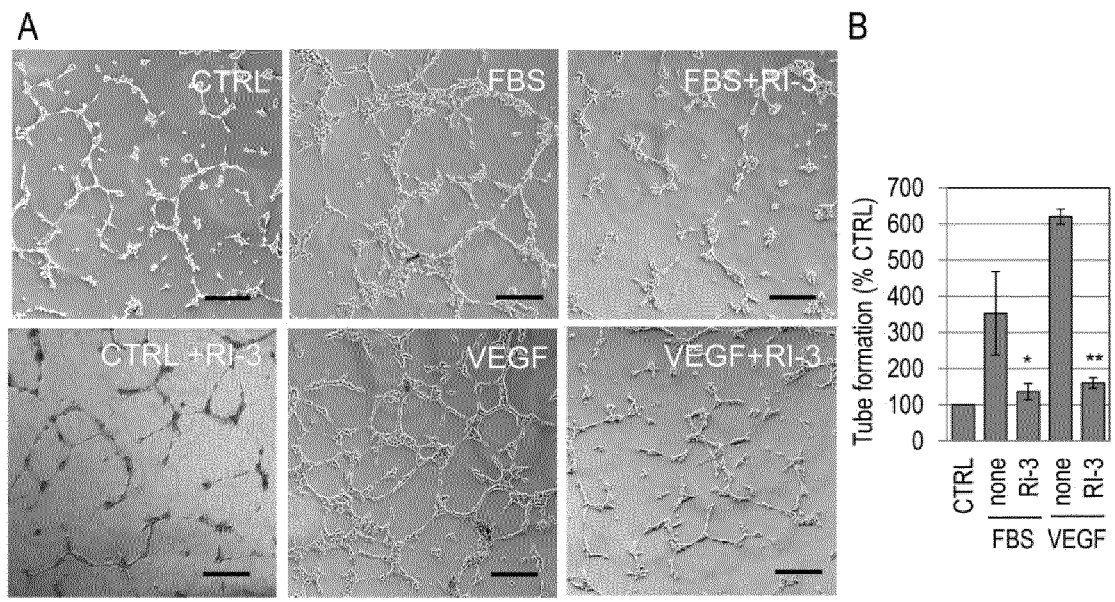
FIG. 10 At the concentration of 10 nM the retro-inverso peptide RI-3 inhibits both FBS (61%) and VEGF-triggered (75%) endothelial tube formation. (A) representative pictures taken with an inverted microscope at 100× magnifications. (B) quantitative analysis (Example 10).
Figure 11:
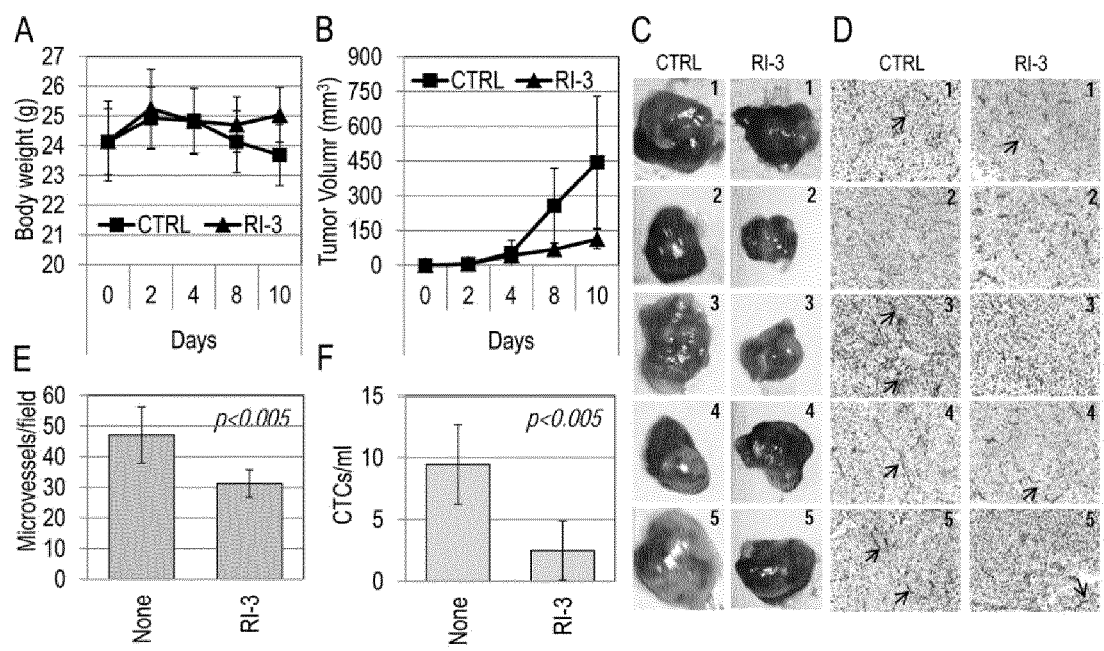
FIG. 11 The intraperitoneal (i.p.) administration of 6 mg/Kg of the retro-inverso peptide RI-3 every day for 10 days reduces in vivo tumor growth and vascular infiltration by human chondrosarcoma Sarc cells in nude mice. (A) Time-dependent average of treated and control mice. (B) Tumor volumes measured at different time points. (C) Tumors excised after 10 days. (D) CD31 immuno-staining of formalin fixed paraffin sections of the excised tumors. (E) Counts of vascular channels harboring red blood cells on CD31 immuno-stained sections. (F) Quantification of Circulating Tumor Cells (CTCs). (Example 11)

The entry of tumor cells into bloodstream is one of the earliest events of the metastatic process. The ability of RI-3 to affect trans-endothelial migration of human chondrosarcoma Sarc (A) melanoma A375 (B), ovarian carcinoma SKOV-3 (C) cells, or THP1 monocytes (D) was monitored by the xCELLigence RTCA system. Human Umbilical Vein Endothelial Cells (HUVEC) ($1\times10^4$ cells/well) suspended in growth medium, were allowed to grow for 20-25 hrs until they form a confluent monolayer, prior to seeding Sarc, A375, SKOV-3, or THP-1 cells ($1\times10^4$ cells/well) in growth medium in the absence (None) or in the presence of 10 nM RI-3. The experiments were performed twice in quadruplicate. When cells cross the endothelial monolayer, there is a drop in electrical resistance which is monitored in real-time for 5 hrs as the cell index changes due to the rupture of endothelial monolayer. The results are reported in FIG. 9. All cell lines were able to reduce endothelial monolayer integrity. The addition of 10 nM RI-3 inhibited the capability of Sarc, A375, SKOV-3, and THP-1 cells to disrupt endothelial monolayers by 17%, 22%, 58%, and 36% respectively.

EXAMPLE 10. RETRO-INVERSO PEPTIDE RI-3 INHIBITS BOTH FBS AND VEGF-TRIGGERED ENDOTHELIAL TUBE FORMATION

Endothelial cells undergo morphological differentiation into an extensive network of capillary-like structures consisting of highly organized three-dimensional cords when seeded on matrigel in the presence of a pro-angiogenic stimuli. HUVECs were suspended in medium (CTRL) or medium with 10% FBS or 40 ng/ml VEGF165, without (None) or with 10 nM RI-3 and seeded on matrigel-coated plates for 6 hrs at 37° C., 5% $CO_2$. Representative pictures were taken with an inverted microscope at 100× magnifications. Scale bar: 10 µm (A). Quantitative analysis of tube formation was calculated as a percentage of tubes formed by cord-like structures counted in the absence of any angiogenic stimulus and considered as 100% (CTRL). Data represent means±SD of two independent experiments performed in duplicate. Statistical significance was calculated against none with *p<0.05, **p<0.001 (B). Both FBS and VEGF promoted endothelial tube formation, reaching 352% and 620%, respectively, above basal. The retro-inverso peptide RI-3 reduced FBS- and VEGF-dependent tube formation by 61% and 75%, respectively.

EXAMPLE 11. RETRO-INVERSO PEPTIDE RI-3 EXERTS ANTI-METASTATIC EFFECT REDUCING IN VIVO TUMOR GROWTH AND VASCULAR INFILTRATION BY SARCOMA CELLS

Ten six-eight week old, CD1 female nude mice received the injection of human Sarc cells as a single-cell suspension ($1\times10^6$ cells in 100 µl PBS, 96% viability) into the right flank. Five animals received i.p-administration of 6 mg/Kg RI-3 every day for 10 days, and five received injections of vehicle only (CTRL). A. Time-dependent average weight was monitored every two days. B. Tumor volumes measured at different time points with a caliper, using the formula: ½×(width)²×length (mm). After 10 days, blood samples (~500 µL/mouse) from the retroorbital venous plexus of mice were collected and processed for determination of Circulating Tumor Cells (CTC)s. Then, animals were sacrificed and the excised tumors (C) were fixed in buffered formalin and processed for paraffin sectioning. Tumor vascularization was assessed by counting vascular channels harbouring red blood cells on CD31 immuno-stained sections (D) in 5 randomly chosen fields per section, in at least two sections per tumor at ×200 (E). To quantify CTCs, DNA from nucleated cells of murine blood samples was purified and quantitated by Real-Time PCR using primers targeting human Alu-sequences. Number of CTCs was calculated by comparing the obtained amplification curves with others generated in spiking experiments, which were included in every run (F).

Sarc cells readily formed tumors when injected subcutaneously in the flanks of the immuno-compromised mice and survived to the treatment schedule without clear changes in body weight (A). The measurement of tumor volume at various time points showed that the kinetics of tumor formation in vehicle-treated mice were significantly higher than those assessed in RI-3 treated mice. Tumor volumes of vehicle- and RI-3-treated mice were 445+/−285 and 112+/−41 $mm^3$, respectively, with p<0.05 (B). After 10 days, animals were sacrificed and tumors excised (C). According with the ability of RI-3 to prevent in vitro formation of a capillary network, the intratumoral microvessel density was reduced in tumors from animals treated with RI-3 as compared to those treated with vehicle alone (D-E). Quantification of CTCs released in the blood of untreated and treated mice revealed the presence of 9.4+/−3 CTCs/mL in blood samples from 5/5 untreated mice and 2.4+/−2 CTCs/mL in blood samples from 3/5 mice treated with RI-3 (F).

REFERENCES

1. Wirtz D, Konstantopoulos K, Searson P C. The physics of cancer: the role of physical interactions and mechanical forces in metastasis. Nat Rev Cancer. 2011; 11:512-22.
2. Friedl, P. & Bröcker, E. -B. The biology of cell locomotion within three-dimensional extracellular matrix. Cell. Mol. Life Sci. 2000; 57:41-64.
3. Mellado M, Martínez-Muñoz L, Cascio G, Lucas P, Pablos J L, Rodríguez-Frade J M. T Cell Migration in Rheumatoid Arthritis. Front Immunol. 2015; 6:384.
4. Pantel, K. and Brakenhoff, R. H. Dissecting the metastatic cascade. Nat Rev Cancer 2004; 4: 448-456.
5. Ridley A J, Schwartz M A, Burridge K, Firtel R A, Ginsberg M H, Borisy G, Parsons J T, Horwitz A R. Cell migration: integrating signals from front to back. Science 2003; 302:1704-9.
6. Lauffenburger, D. A. & Horwitz, A. F. Cell migration: a physically integrated molecular process. Cell 1996; 84:359-369.
7. Ridley A J. Life at the leading edge. Cell 2011; 145:1012-22.
8. Lund I K, Illemann M, Thurison T, Christensen I J, Høyer-Hansen G. uPAR as Anti-Cancer Target: Evaluation of Biomarker Potential, Histological Localization, and Antibody-Based Therapy. Current Drug Targets 2011; 12: 1744-60.
9. Blasi F. Upa, upar, pai-1: Key intersection of proteolytic, adhesive and chemotactic highways? Immunology today 1997; 18:415-7.
10. Ploug M, Ronne E, Behrendt N, Jensen A L, Blasi F, Dario K. Cellular receptor for urokinase plasminogen activator. Carboxyl-terminal processing and membrane anchoring by glycosyl-phosphatidylinositol. J Biol Chem 1991; 266:1926-33.
11. Ploug M, Ellis V. Structure-function relationships in the receptor for urokinase-type plasminogen activator—comparison to other members of the Ly-6 family and snake venom α-neurotoxins. FEBS Lett 1994; 349:163-8.
12. Kjaergaard M, Hansen L V, Jacobsen B, Gardsvoll H, Ploug M. Structure and ligand interactions of the urokinase receptor (uPAR). Front Biosci 2008; 13:5441-61.
13. Sidenius N, Blasi F. The urokinase plasminogen activator system in cancer: recent advances and implication for prognosis and therapy. Cancer Metastasis Rev 2003; 22: 205-22.
14. Carriero M V, Stoppelli M P. The urokinase-type plasminogen activator and the generation of inhibitors of urokinase activity and signaling. Curr Pharm Des 2011; 17: 1944-61.
15. Gargiulo L, Longanesi-Cattani I, Bifulco K, Franco P, Raiola R, Campiglia P, Grieco P, Peluso G, Stoppelli M P, Carriero M V. Cross-talk between fMLP and vitronectin receptors triggered by urokinase receptor-derived SRSRY peptide. J Biol Chem 2005; 280: 25225-32.
16. Bifulco K, Longanesi-Cattani I, Gala M, D I Carluccio G, Masucci M T, Pavone V, Lista L, Arra C, Stoppelli M P, Carriero M V. The soluble form of urokinase receptor promotes angiogenesis through its $Ser^{88}$-Arg-Ser-Arg-$Tyr^{92}$ chemotactic sequence. J Thromb Haemost 2010; 8: 2789-99.
17. Le Y, Murphy P M, Wang J M. Formyl-peptide receptors revisited. Trends Immunol 2002; 23:541-8.
18. Ye R D, Boulay F, Wang J M, Dahlgren C, Gerard C, Parmentier M, Serhan C N, Murphy P M. International Union of Basic and Clinical Pharmacology. LXXIII Nomenclature for the formyl peptide receptor (FPR) family. Pharmacol Rev 2009; 61:119-61.
19. Panaro M A, Acquafredda A, Sisto M, Lisi S, Maffione A B, Mitolo V. Biological role of the N-formyl peptide receptors. Immunopharmacol Immunotoxicol 2006; 28:103-27.
20. Chakravarti N1, Peddareddigari V G, Warneke C L, Johnson M M, Overwijk W W, Hwu P, Prieto V G. Differential expression of the G-protein-coupled formyl Peptide receptor in melanoma associates with aggressive phenotype. Am J Dermatopathol 2013; 35:184-90.
21. Liang Zhang, Huanyu Wang, Tianshu Yang, Zhifeng Su, Dan Fang, Yafeng Wang, Jiazhu Fang, Xinwei Hou, Yingying Le, Keqiang Chen, Ji Ming Wang, Shao Bo Su, Qing Lin, Qi Zhou. Formylpeptide receptor 1 mediates the tumorigenicity of human hepatocellular carcinoma cells. OncoImmunology Vol. 5, Iss. 2, 2016.
22. Liu M, Zhao J, Chen K, Bian X, Wang C, Shi Y, Wang J M. G protein-coupled receptor FPR1 as a pharmacologic target in inflammation and human glioblastoma. Int Immunopharmacol 2012; 14:283-8.
23. Bifulco K, Longanesi-Cattani I, Gargiulo L, Maglio O, Cataldi M, De Rosa M, Stoppelli M P, Pavone V, Carriero M V. An urokinase receptor antagonist that inhibits cell migration by blocking the formyl peptide receptor. FEBS Lett 2008; 582: 1141-6.
24. Carriero M V, Longanesi-Cattani I, Bifulco K, Maglio O, Lista L, Barbieri A, Votta G, Masucci M T, Arra C, Franco R, De Rosa M, Stoppelli M P, Pavone V. Structure-based design of an urokinase-type plasminogen activator receptor-derived peptide inhibiting cell migration and lung metastasis. Mol Cancer Ther 2009; 8: 2708-17.
25. Bifulco K, Longanesi-Cattani I, Liguori E, Arra C, Rea D, Masucci M T, De Rosa M, Pavone V, Stoppelli M P, Carriero M V. A Urokinase Receptor-Derived Peptide Inhibiting VEGF-Dependent Directional Migration and Vascular Sprouting. Mol Cancer Ther 2013; 12: 1981-1993.
26. Carriero M V, Bifulco K, Minopoli M, Lista L, Maglio O, Mele L, Di Carluccio G, De Rosa M, Pavone V. UPARANT: a urokinase receptor-derived peptide inhibitor of VEGF-driven angiogenesis with enhanced stability and in vitro and in vivo potency. Mol Cancer Ther 2014; 13: 1092-104.
27. Chorev M, Goodman M. Recent developments in retro peptides and proteins—an ongoing topochemical exploration. Trends Biotechnol. 1995; 13: 438-45.
28. Fletcher M D, Campbell M M. Partially Modified Retro-Inverso Peptides: Development, Synthesis, and Conformational Behavior. Chem Rev 1998; 98: 763-796.
29. Mason J M. Design and development of peptides and peptide mimetics as antagonists for therapeutic intervention. Future Med. Chem. 2010; 2: 1813-22.
30. Chorev M. The partial retro-inverso modification: a road traveled together. Biopolymers 2005; 80: 67-84.
31. Carver J A, Esposito G, Viglino P, Fogolari F, Guichard G, Briand J P, Van Regenmortel M H, Brown F, Mascagni P. Structural comparison between retro-inverso and parent peptides: molecular basis for the biological activity of a retro-inverso analogue of the immunodominant fragment of VP1 coat protein from foot-and-mouth disease virus. *Biopolymers* 1997; 41: 569-90.
32. Pescarolo M P, Bagnasco L, Malacarne D, Melchiori A, Valente P, Millo E, Bruno S, Basso S, Parodi S. A retro-inverso peptide homologous to helix 1 of c-Myc is a potent and specific inhibitor of proliferation in different cellular systems. *FASEB J.* 2001; 15: 31-33.
33. Parthsarathy V, McClean P L, Holscher C, Taylor M, Tinker C, Jones G, Kolosov O, Salvati E, Gregori M, Masserini M, Allsop D. A novel retro-inverso peptide inhibitor reduces amyloid deposition, oxidation and inflammation and stimulates neurogenesis in the APPswe/PS1DeltaE9 mouse model of Alzheimer's disease. *PLoS One* 2013; 8: e54769.
34. Matharu B, El-Agnaf O, Razvi A, Austen B M. Development of retro-inverso peptides as anti-aggregation drugs for beta-amyloid in Alzheimer's disease. *Peptides* 2010; 31: 1866-72.
35. Li Y, Lei Y, Wagner E, Xie C, Lu W, Zhu J, Shen J, Wang J, Liu M. Potent Retro-Inverso d-Peptide for Simultaneous Targeting of Angiogenic Blood Vasculature and Tumor Cells. *Bioconjug. Chem.* 2012; 24: 133-143.
36. Acerra N, Kad N M, Griffith D A, Ott S, Crowther D C, Mason J M. Retro-inversal of Intracellular Selected β-Amyloid-Interacting Peptides: Implications for a Novel Alzheimer's Disease Treatment. *Biochemistry* 2014; 53: 2101-2111.
37. Bonelli F, Pessi A, Verdini A S. Solid phase synthesis of retro-inverso peptide analogues. Synthesis and biological activity of the partially modified retro-inverso analogue of the bradykinin potentiating peptide BPP9a [gLys6, (RS)-mPhe7, Ala8] BPP9a. *Int. J. Pept. Prot. Res.* 1984; 24: 553-6.
38. Chorev M, Rubini E, Gilon C, Wormser U, Selinger Z. Synthesis of partially modified retro-inverso substance P analogues and their biological activity. *J. Med. Chem.* 1983; 26: 129-35.
39. Chorev M, Shavitz R, Goodman M, Minick S, Guillemin R. Partially modified retro-inverso-enkephalinamides: topochemical long-acting analogs in vitro and in vivo. *Science* 1979; 204: 1210-2.
40. Durr H, Wieland H, Beck-Sickinger A G, Jung G, *Retro-inverso analogs of neuropeptide Y*, in *Peptides* 1992, C. H. Schneider and A. N. Eberle, Editors. 1992, ESCOM Science Publishers B.V. p. 609-610.
41. Taylor M, Moore S, Mayes J, Parkin E, Beeg M, Canovi M, Gobbi M, Mann D M, Allsop D. Development of a proteolytically stable retro-inverso peptide inhibitor of beta-amyloid oligomerization as a potential novel treatment for Alzheimer's disease. *Biochemistry* 2010; 49: 3261-72.

The invention claimed is:

1. A compound
selected from the group consisting of:
Ac-(D)-Tyr-(D)-Arg-(D)-Glu-(D)-Arg-NH$_2$ (RI-1);
Ac-(D)-Tyr-(D)-Arg-Aib-(D)-Arg-NH$_2$ (RI-3);
PhCH$_2$CO-(D)-Arg-Aib-(D)-Arg-NH$_2$ (RI-4);
PhCH$_2$CH$_2$CO-(D)-Arg-Aib-(D)-Arg-NH$_2$ (RI-5);
and their pharmaceutically acceptable salts.

2. The compound according to claim 1 in association with vehicles and/or excipients.

3. The compound according to claim 1 radiolabeled with a positron emitter for microPET imaging.

4. The compound according to claim 3 in association with vehicles and/or excipients.

5. A method of treating cancer in patients in need thereof with a medicament comprising a compound according to claim 1, said method comprising administering said compound to said patients.

6. The method according to claim 5, wherein the cancer comprises local or metastatic invasion of malignant tumors.

7. A method of treating chronic inflammation in patients in need thereof with the compound according to claim 1, said method comprising administering said compound to said patients.

8. A method of treating disorders related to neo-angiogenesis and neo-vascularization in patients in need thereof with the compound according to claim 1, said method comprising administering said compound to said patients.

* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Tyr is D-Tyr
<220> FEATURE:
<221> NAME/KEY: MOD_RES
<222> LOCATION: (2)..(2)
<223> OTHER INFORMATION: Arg is D-Arg
<220> FEATURE:
<221> NAME/KEY: MOD_RES
<222> LOCATION: (3)..(3)
<223> OTHER INFORMATION: Glu is D-Glu
<220> FEATURE:
<221> NAME/KEY: MOD_RES
<222> LOCATION: (4)..(4)
<223> OTHER INFORMATION: Arg is D-Arg

<400> SEQUENCE: 1

Tyr Arg Glu Arg
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (1)..(1)
<223> OTHER INFORMATION: Tyr is D-Tyr
<220> FEATURE:
<221> NAME/KEY: MOD_RES
<222> LOCATION: (2)..(2)
<223> OTHER INFORMATION: Arg is D-Arg
<220> FEATURE:
<221> NAME/KEY: MOD_RES
<222> LOCATION: (3)..(3)
<223> OTHER INFORMATION: Ser is D-Ser
<220> FEATURE:
<221> NAME/KEY: MOD_RES
<222> LOCATION: (4)..(4)
<223> OTHER INFORMATION: Arg is D-Arg

<400> SEQUENCE: 2

Tyr Arg Ser Arg
1

<210> SEQ ID NO 3
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Tyr is D-Tyr
<220> FEATURE:
<221> NAME/KEY: MOD_RES
<222> LOCATION: (2)..(2)
<223> OTHER INFORMATION: Arg is D-Arg
<220> FEATURE:
<221> NAME/KEY: MOD_RES
<222> LOCATION: (3)..(3)
<223> OTHER INFORMATION: X is Aib
<220> FEATURE:
<221> NAME/KEY: MOD_RES
<222> LOCATION: (4)..(4)
<223> OTHER INFORMATION: Arg is D-Arg

<400> SEQUENCE: 3

Tyr Arg Xaa Arg
1
```